United States Patent [19]
Ürögdi et al.

[11] Patent Number: 6,002,002
[45] Date of Patent: Dec. 14, 1999

[54] ANTI-ISCHAEMIC HYDROXYLAMINE DERIVATIVES AND PHARMACEUTICAL COMPOSITIONS

[75] Inventors: László Ürögdi; Ede Márványos; Mihály Barabás; László Jaszlits; Katalin Bíró, all of Budapest; Andrea Jednákovits, Szentendre; Erzsébet Radványné, Csalogány; Mária Kürthy; Istvánné Udvardy Nagy, both of Budapest, all of Hungary

[73] Assignee: Biorex Research & Development Co., Veszprem-Szabadsagpuszta, Hungary

[21] Appl. No.: 08/914,115

[22] PCT Filed: Jun. 14, 1996

[86] PCT No.: PCT/HU96/00033

§ 371 Date: May 13, 1998

§ 102(e) Date: May 13, 1998

[87] PCT Pub. No.: WO97/00251

PCT Pub. Date: Jan. 3, 1997

[30] Foreign Application Priority Data

Jun. 15, 1995 [HU] Hungary .................... 05 01756

[51] Int. Cl.$^6$ .................... C07D 211/08; C07D 241/04; C07D 265/30; C07C 239/04
[52] U.S. Cl. .................... 544/171; 544/399; 544/400; 546/192; 564/297; 564/299; 564/301
[58] Field of Search .................... 564/301, 299, 564/297; 514/640, 253; 546/192; 544/399, 400, 171

[56] References Cited

U.S. PATENT DOCUMENTS

4,404,384  9/1983  Gebert et al. .................... 544/394

FOREIGN PATENT DOCUMENTS

2059184      7/1992  Canada .................... C07D 211/40
0 495 750 A2 1/1992  European Pat. Off. .
0369944      9/1989  Germany .................... A61K 31/15

OTHER PUBLICATIONS

2–Substituted 3–(Aminooxy) propanamines as inhibitors of Ornithine Decarboxylose: Synthesis and Biological Activity, *J. Med. Chem*, 1992, 35, 1339–1344.

Lipid metabolism of the Heart and Arteries in Relation to Ischemic Heart Disease, (L.H. Opie), *The Lancet*, Jan. 27, 1973, p. 192–195.

The Synthesis of Hydroxylamine Derivatives Possessing Hypocholesteremic Activity, (B.J. Ludwig et al), *Ludwig, Dursch, Auerbach, Tomeczek and Berger*, Jul., 1967.

Chemical Abstracts, vol. 67, 1967 P. 6887, Abstract No. 73271g.

International Search Report, International Application PCT/HU 96/00033, Nov. 8, 1996, 3 pages.

Alfred Burger, A guide to the Chemical Basis of Drug Design. p. 15, 1.3.1 Pro–Drugs, Jan. 13, 1983.

*Primary Examiner*—Alan L. Rotman
*Assistant Examiner*—Rita Desai
*Attorney, Agent, or Firm*—Duane, Morris & Heckscher LLP

[57] ABSTRACT

The present invention provides novel hydroxylamine derivatives represented by the general formula:

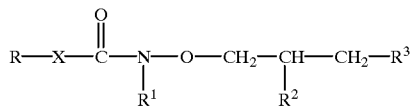

wherein:

X is O, —NH, or a group of formula NR', wherein R and R' are independently selected from alkyl, cycloalkyl, phenylalkyl, phenyl optionally substituted with halo, haloalkyl, alkyl, alkoxy or nitro; and a N-containing heterocyclic ring;

$R^1$ is H or alkanoyl, $R^2$ is H or hydroxy optionally acylated with alkanoyl, and $R^3$ is a group of the formula —$NR^4R^5$ wherein $R^4$ and $R^5$ are independently selected from H, alkyl, and a group of the formula —CO—NH—R wherein R is as defined above, or wherein $R^4$ and $R^5$ when taken together form a 5- to 7-membered heterocyclic ring which may optionally contain one additional hetero atom selected from nitrogen, oxygen and sulfur and which is optionally substituted with alkyl or phenylalkyl.

Also provided are pharmaceutically acceptable acid addition salts of the compounds defined above, as well as pharmaceutical compositions containing the compounds or their acid addition salts as active ingredients. The compounds of the invention have been shown to have anti-ischemic effects.

8 Claims, No Drawings

ANTI-ISCHAEMIC HYDROXYLAMINE DERIVATIVES AND PHARMACEUTICAL COMPOSITIONS

CROSS-REFERENCE

This application is a 371 of PCT/Hu96/00033 filed on Jun. 14, 1996.

TECHNICAL FIELD

The invention relates to novel hydroxylamine derivatives represented by the general formula (I),

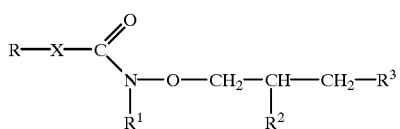

(I)

the pharmaceutically acceptable acid addition salts thereof as well as the pharmaceutical compositions containing the same as active ingredient. Another object of the invention is the preparation of the hydroxylamine derivatives and salts thereof.

The compounds according to the invention possess anti-ischaemic effect.

BACKGROUND ART

Compounds of similar structure have been described in C.A. 67 (p. 6886) 73271 g and C.A. 113 (p. 674) 171694k.

DISCLOSURE OF INVENTION

One object of the present invention is the group of hydroxylamine derivatives represented by the general formula (I) and the pharmaceutically acceptable acid addition salts thereof. In the above formula X is O, —NH or a group of the formula —NR'—, wherein
  R and R', independently from each other, are alkyl, cycloalkyl, phenylalkyl; a phenyl group optionally substituted with halo, haloalkyl, alkyl, alkoxy or nitro; or an N-containing hetero ring,
$R^1$ is H or alkanoyl,
$R^2$ is H or hydroxy optionally acylated with alkanoyl, and
$R^3$ is a group of the formula —N($R^4$)$R^5$ wherein
  $R^4$ and $R^5$, independently from each other, may be H. alkyl or a group of the formula —C(O)—NH—R wherein R is as defined above, or, $R^4$ and $R^5$, when taken together with the adjacent nitrogen attached thereto, form a 5 to 7-membered hetero ring which may contain one additional hetero atom selected from nitrogen, oxygen and sulfur and which is optionally substituted with alkyl of phenylalkyl.

Another object of the invention is a pharmaceutical composition which contains at least one of the compounds of the general formula (I) or the pharmaceutically active acid addition salt thereof as active ingredient.

Still another object of the invention is a plurality of processes for preparing the compounds of the general formula (I) and the pharmaceutically acceptable acid addition salts thereof. Though these compounds may be prepared by any process known in the art for preparing compounds of similar structure, the most favorable methods to obtain the same include the followings:

a) for preparing compounds of the general formula (I) wherein X is O, i) a compound of the general formula (II)

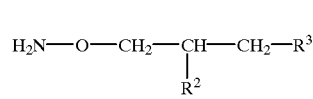

(II)

wherein $R^2$ and $R^3$ are as defined above, is reacted with a compound of the general formula (III)

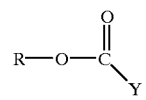

(III)

wherein R is as defined above and Y is halo or azido, or ii) a compound of the general formula (VI)

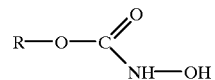

(VI)

is reacted with a compound of the general formula (VII)

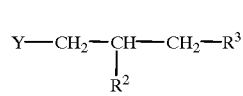

(VII)

or iii) a compound of the general formula (VI) is reacted with a compound of the general formula (VIII)

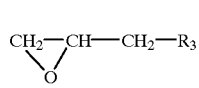

(VIII)

or iv) a compound of the general formula (VI) is reacted with a compound of the general formula (IX)

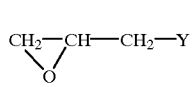

(IX)

and subsequently with a compound of the formula $R^3$H, wherein in the formulae (VI), (VII), (VIII) and (IX) R, $R^2$ and $R^3$ are as defined above and Y is halo, b) for preparing compounds of the general formula (I) wherein X is —NH—, a compound of the general formula (II) wherein $R^2$ and $R^3$ are as defined above, is reacted with a compound of the formula (IV) or (IVa)

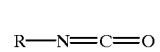

(IV)

-continued

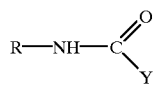
(IVa)

wherein R is as defined above and Y is halo, or c) for preparing compounds of the general formula (I) wherein X is —NH— or —NR'—, a compound of the general formula (X)

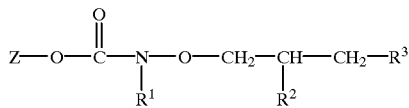
(X)

wherein $R^1$, $R^2$ and $R^3$ are as defined above and Z is alkyl, aralkyl or optionally substituted aryl, is reacted with a compound of the general formula $RNH_2$ or RR'NH, wherein R and R' are as defined above, or d) for preparing compounds of the general formula (I) wherein X is —NH—, $R^3$ is —$N(R^4)R^5$, $R^4$ is alkyl and $R^5$ is —C(O)—NH—R,
  i) a compound of the formula (II) wherein $R^3$ is —$N(R^4)R^5$, $R^4$ is alkyl $R^5$ is H, and R$^2$ is as defined above, is reacted with an excess of a compound of the formula (IV) or (IVa) wherein R is as defined above and Y is halo, or
  ii) a compound of the general formula (I) wherein $R^3$ is —$N(R^4)R^5$, $R^4$ is alkyl, $R^5$ is H and $R^1$, $R^2$ and $R^3$ are as defined above, is reacted with a compound of the general formula (IV) or (Iva) wherein R is as defined above and Y is halo, or e) for preparing compounds of the general formula (I) wherein X is —NR'—, a compound of the general formula (II) is reacted with a compound of the general formula (V)

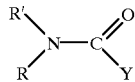
(V)

wherein R, R', $R^2$ and $R^3$ are as specified above and Y is halo, and, if desired, a compound of the general formula (I) is transformed in its acid addition salt, or if desired, a compound of the general formula (I) wherein $R^1$ is H and $R^2$ is hydroxy, is transformed into a compound of the general formula (I) wherein $R^2$ is acyloxy or $R^1$ is acyl and $R^2$ is acyloxy, optionally followed by salt forming.

Best Mode for Carrying out the Invention

Preferred representatives of the different groups defined are as follows:

The alkyl groups and the alkyl parts of the alkanoyl groups mentioned in the specification can be straight or branched, lower or longer alkyl moieties.

The alkyl group, either standing alone or forming part of any of the above groups, may preferably contain 1 to 12 carbon atoms. Preferably, the number of carbon atoms is 1 to 8. Examples of such group include, among others, methyl, ethyl, propyl, isopropyl, butyl, isobutyl, sec.butyl, pentyl, hexyl, heptyl, octyl and the isomers thereof. Preferred are the alkyl groups with 1 to 6 carbon atoms such as methyl, ethyl, propyl, isopropyl, butyl, isobutyl, sec.butyl, pentyl, tert.pentyl and hexyl.

The preferred longer alkyl groups contain 9 to 21 carbon atoms such as iso- or n-nonyl, decyl, undecyl, dodecyl, tridecyl, tetradecyl, pentadecyl, hexadecyl, heotadecyl, octadecyl, nonadecyl, eicosyl and heneicosyl and the like; more preferably the $C_{9-17}$ alkyl groups such as iso- or n-nonyl, decyl, undecyl, dodecyl, tridecyl, tetradecyl, pentadecyl, hexadecyl and heptadecyl.

The cycloalkyl group contains preferably 3 to 8, most preferably 5 to 7 carbon atoms. Such groups are e.g. cyclopropyl, cyclobutyl, cyclopentyl, cyclohexyl, cycloheptyl, cyclooctyl and the like; most preferred are the $C_{3-7}$ cycloalkyl groups, such as cyclopropyl, cyclobutyl, cyclopentyl, cyclohexyl and cycloheptyl.

The N-containing heteroaromatic ring is preferably a 3 to 8-membered, preferably 5 or 6-membered heteromonocyclic group which is unsaturated and contains 1 to 4 nitrogen atoms. Such groups are e.g. pirrolyl, imidazolyl, pirazolyl, piridyl, or the N-oxide thereof, pirimidinyl, pirazinyl, piridazinyl, triazolyl, tetrazolyl, triazinyl or the like; or it may be a condensed heterocyclic group containing 1 to 5 nitrogen atoms, such as indolyl, isoindolyl, indolisinyl, benzimidazolyl, quinolyl, isoquinolyl, indazolyl, benztriazolyl, cinnolyl, phtalazinyl, quinazolinyl, quinoxalinyl, purinyl, pteridinyl, quinolizinyl, naphtiridinyl and the like.

The 5 to 7-membered unsaturated heterocyclic groups may also contain one nitrogen and additional nitrogen, oxygen or sulfur atom or atoms. These groups are preferably aziridinyl, azetidinyl, oxaziridinyl, oxazolidinyl, thiazolidinyl, pirrolidinyl, imidazolidinyl, pirazolidinyl, perhydrothiazolyl, perhydroisoxalolyl, piperidinyl, piperazinyl, perhydropirimidinyl, morpholinyl, thiomorpholinyl, perhydro-1H-azepinyl and the like.

The alkanoyl group may contain both lower or higher chain and may be preferably $C_{1-6}$, preferably $C_{1-4}$ alkyl-carbonyl, e.g. acetyl, propanoyl or the like, or the acyl group of a higher, preferably $C_{12-18}$ fatty acid.

$R^4$ and $R^5$ together with the adjacent nitrogen atom form preferably saturated heterocyclic groups, e.g. pirrolidino, oxazolidino thiazolidino, piperidino, morpholino, piperazino, thiomorpholino, azepino and the like.

According to process a) carbamates of the general formula (I) wherein X is O are prepared by reacting the suitable starting materials. The reaction according to process a), variant i) is preferably carried out in an inert organic solvent, at about 0° C., while the other variants are preferably performed at elevated temperatures.

According to process b) ureas of the general formula (I) wherein X is —NH— are prepared by reacting the corresponding compounds of the formulae (II) and (IV) or (IVa) wherein R is as defined above and Y is halo. The reaction is carried out preferably in an inert organic solvent, at ambient temperature.

According to process c) compounds of the general formula (I) wherein X is —NH— or —NR'— are prepared by reacting the compounds of the formula (X) and an amine of the formula $RNH_2$ or RR'NH. The reaction is carried out preferably in an inert organic solvent, at elevated temperature.

According to process d) ureas of the general formula (I) wherein X is —NH— are prepared wherein $R^3$ is —$N(R^4)$ $R^5$, and $R^4$ is alkyl and $R^5$ is a group of the formula —C(O)—NHR.

In this reaction a compound of the formula (II) wherein $R^4$ is alkyl and $R^5$ is H is used as starting material wherein 1 mol of this material is reacted with at least two moles of the compounds of the general formulae (IV) or (IVa). The reaction is preferably carried out in an organic solvent, at ambient temperature.

According to process e) ureas of the general formula (I) wherein X is —NR'— are prepared by reacting the corresponding compounds of the formulae (II) and (IV) wherein R is as defined above. The reaction is carried out preferably in an inert organic solvent, at ambient temperature.

If desired, a compound of the general formula (I) can be transformed into the monoacylated ($R^2$=acyloxy) or diacylated ($R^1$=acyl, $R^2$=acyloxy) derivative. Acylation is carried out preferably with a corresponding derivative of suitably $C_{2-8}$ aliphatic carboxylic acids capable of acylating.

The pharmaceutically acceptable salts of the compounds of the general formula (I) may be those formed with both organic and inorganic salts.

The compounds according to the invention possess antiischaemic effect.

The reperfusion-induced arrhytmia (ventricular tachycardia, KT and ventricuiar fibrillation, KF) was tested on anaesthetized rats. Myocardial ischaemia was induced by pressing the coronary artery for 5 minutes followed by 10 minutes reperfusion of the heart. The ECG was permanently monitored and the change of mean period of KT and KF by the effect of active materials was measured in the first 3 minutes of reperfusion. Survival was also monitored. The compounds were administered i.v. 5 minutes before pressing the LAD coronary artery in a dosis of 1 mg/kg.

Experimental results obtained by administering some representative compounds of the invention are listed below:

| Example No. | 4 | 5 | 6 | 7 | 15 | 16 | 23 | Untreated control |
|---|---|---|---|---|---|---|---|---|
| Survival % | 67 | 67 | 100 | 86 | 60 | 83 | 80 | 0 |

The vasorelaxant effect of the compounds of the invention was tested in vitro on isolated rabbit thoracal aorta according to Am. J. Physiol. 257:, 1327–1333 (1989).

The aggregation inhibitory effect was demonstrated on venal blood samples obtained from human patients. To the samples sodium citrate was added and 10 minutes later centrifuged with 1000 rpm. In the platelet-rich praparates thus obtained platelet aggregation was induced by the addition of ADP (control) while the different concentrations of the test compounds were added to the preparates before the addition of ADP, the dosis-effect curve was demonstrated and the concentrations inhibiting the aggregation in 50% ($ED_{50}$) were determined.

Experimental results obtained by the addition of some representative compounds of the invention are listed below:

| | in vitro | |
|---|---|---|
| No. of compound | vasorelaxation $EC_{50}$ (mol) | antiaggregation $EC_{50}$ (mol) |
| 6. | $1.9 \times 10^{-4}$ | $1.5 \times 10^{-3}$ |
| 7. | $1.0 \times 10^{-4}$ | $0.9 \times 10^{-3}$ |
| 16. | $4.5 \times 10^{-4}$ | $0.71 \times 10^{-3}$ |
| 19. | $3.8 \times 10^{-5}$ | $0.34 \times 10^{-3}$ |
| 23. | $1.9 \times 10^{-4}$ | $0.43 \times 10^{-3}$ |
| Reference material | (1) $8.3 \times 10^{-5}$ | (2) $1.5 \times 10^{-3}$ |

(1) Bepridyl [Eur. J. Pharm. 166: (1989) 241–49]
(2) Molsidomin (Takeda)

The invention is illustrated more in details by the following examples. However, the examples serve only to provide more information on the invention and no way to limit the scope of protection thereto.

EXAMPLE 1

N-phenyl-N'-(2-hydroxy-3-piperidino-propoxy)-urea

O-(2-hydroxy-3-piperidino-propyl)-hydroxylamine (1,74 g, 0,01 mol) was dissolved in 40 ml chloroform and 1,09 ml (0,01 mol) phenyl isocyanate was added thereto while stirring. The reaction was monitored by chromatography. After the end of reaction the solution was evaporated and the oily residue was purified by column chromatography. The oil thus obtained was crystallized from diethyl ether. Yield: 0,6 g (20%). Mp: 101–103° C.

IR(KBr): 3288, 2935, 1678, 1601, 1551, 1501, 1448, 1333, 1250, 1094, 1038, 903, 866, 754, 694 cm$^{-1}$. $^1$H-NMR (CDCl$_3$): 8,95 (1H,br,s,CONHO); 8,5–7,6 (1H,br,s, N HCONHO); 7,55 (2×1H,t,J=7,3 Hz), 7,27 (2×1H,t), and 7,05 (1H,t,J=7,3 Hz)(phenyl o-m-p); 4,05 (1H,m,CH—OH); 3,96–3,77 (1H, dd, J=11.1 and =2,4 Hz; 1H,dd,J=11,1 and =7,6 Hz,OCH$_2$); 2,7–2,2 (6H,m), 1,55 (4H,m), and 1,46 (2H,m,)(piperidine). $^{13}$C-NMR (CDCl$_3$):158,5 (s,C=O); 138,2 (s), 128,8 (d), 119.3 (d) es 123,2 (d)(phenyl i-o-m-p); 79,4 (t,OCH$_2$); 64,0 (d,CH—OH); 59,8 (t,CH—CH$_2$—N); 54,5 (t), 25,8 (t), and 24,0 (t)(piperidine) Analysis: $C_{15}H_{23}N_3O_3 \cdot 0,5$ H$_2$O: Calculated: C, 59,0%; H, 7,5%; N, 14,0% Found: C 59,6%; H, 7,9%; N, 13,9%.

EXAMPLE 2

N-(2-hydroxy-3-piperidino-propoxy)-ethyl-carbamate

O-(2-hydroxy-3-piperidino-propyl)-hydroxylamine (1,74 g, 0,01 mol) was dissolved in 40 ml chloroform under stirring and 0,95 ml (0,01 mol) ethyl chloroformate in 10 ml chloroform was added thereto dropwise at 0° C. After 1 hour the reaction mixture was washed with 40 ml of 10% sodium carbonate solution and the organic layer was dried over magnesium sulfate. After filtering and evaporating, the crude product thus obtained was purified by column chromatography. The oil thus obtained was crystallized from ether. Yield: 0,75 g (30%). Mp.: 108–110° C.

IR (KBr): 3225, 2943, 2654, 2542, 1739, 1458, 1379, 1331, 1256, 1171, 1115, 1059, 974, 955, 862 cm$^{-1}$. $^1$H-NMR (CDCl$_3$): 10,6 (2×1H,br,NH+OH); 4,50 (1H,m,CH—OH); 4,17 (2H,c, J=7,1 Hz,CH$_3$CH$_2$); 3,92–3,86 (1H,dd,J=10,6 and =4,8 Hz; 1H, dd, J=10,6 and =5.7 Hz,OCH$_2$); 3,27–3,05 (1H,dd,J=13,2 and =1,7 Hz; 1H, dd, J=13,2 and =9,1 Hz,CH— CH$_2$—N); 3,20 ($^4$H,m), 1,96 (4H,m), and 1,65 (2H,m) (piperidine); 1,27 (3H,t,J=7,1 Hz, CH$_3$). $^{13}$C-NMR (CDCl$_3$): 158,2 (s,C=O); 77,8 (t,OCH$_2$); 63,8 (d,CH—OH); 61,9 (t) and 60,5 (t)(CH$_3$CH$_2$+CH—CH$_2$—N); 54,5 (t), 23,2 (t) and 22,1 (t) (piperidine); 14,5 (q,CH$_3$). Analysis:

$C_{11}H_{22}N_2O_4 \cdot 2 H_2O$: Calculated: C, 46,8%; H, 7,9%; N, 9,9% Found: C, 47,4%; H, 8,0%; N, 9,8%.

The above compound was also be prepared by two alternative processes:

I) 1,68 g (0,03 mol) potassium hydroxide was dissolved in 30 ml ethanol and 1,05 g (0,01 mol) N-hydroxyurethane was added thereto. After half hour stirring, 1,62 g(0,01 mol) of 1-chloro-3-piperidino-2-propanol in 10 ml ethanol was added therein dropwise, and the mixture was boiled for 6 hours. The potassium chloride precipitate was filtered off, the solution evaporated and the crude product thus obtained was purified by column chromatography. Crystallizing the oil from the chromatography from ether resulted the title compound. Yield: 1,42 g (58%).

II) 5,25 g (0,05 mol) N-hydroxyurethane was dissolved in 50 ml pure and dry dimethyl formamide followed by the addition of 1,0 g (0,025 mol) pulverized sodium hydroxide and 4,7 ml (0,05 mol) tertiary butanol. To the suspension thus obtained 7,8 g (0,055 mol) of N-(2,3-epoxypropyl)-piperidine [J.A.C.S. 80:, 1257–9 (1958)] was added at 50° C. while stirring. The stirring was continued for 4 hours at 80° C. followed by evaporating in vacuo. The residue was taken up in 50 ml ethanol, the sodium chloride precipitate filtered off and the crude product was purified by column chromatography. After crystallizing from ether, the title compound was obtained. Yield: 8,9 g (72%).

EXAMPLE 3

N-isopropyl-N'-(2-hydroxy-3-piperidino-propoxy)-urea

O-(2-hydroxy-3-piperidino-propyl)-hydroxylamine (1,74 g, 0,01 mol) was dissolved in 25 ml abs. chloroform and under stirring, 0,98 ml (0,01 mol) isopropyl isocyanate was added. The reaction was monitored by chromatography. At the end of the reaction the solution was evaporated and the oily residue purified by column chromatography. The oil thus obtained was crystallized with methanol-ether.

Yield: 1,0 g (39%. Mp.:78–79° C. (from methanol-ether). IR (KBr): 3242, 3055, 2938, 2953, 2012, 1651, 1584, 1486, 1387, 1310 1177, 1090, 1059, 1043, 949 cm$^{-1}$. $^1$H-NMR (DMSO-d$_6$): 8,98 (1H,s,CONH), 6,76 (1H,d,J=7,9 Hz,CHN$\underline{H}$CO); 5,02 (1H,s,OH); 3,95–3,65 (3H,m,C$\underline{H}$NH,C$\underline{H}$OH,OC$\underline{H}_2$); 3,55 (1H,dd,J=10:5 and =7,5 Hz,OCH$_2$); 2,35 (4H,m,piperidine); 2,27 (2H,d,J=6,3 Hz,C$\underline{H}_2$N); 1,6–1,3 6H,m,piperidine); 1,1 (6H,d,J=6,6 Hz,(CH$_3$)$_2$) $^{13}$C-NMR (DMSO-d$_6$): 159,2 (s,C=O); 79,1 (t,OCH$_2$); 65,2 (d,CHOH); 61,3 (t,CH$\underline{C}$H$_2$N); 54,5 (t,piperidine); 40,5 (d,CH(CH$_3$)$_2$); 25,4 (t), and 23,7 (t)(piperidine); 22,6 (q,CH$_3$); 22,5 (q,CH$_3$). Analysis: C$_{12}$H$_{25}$N$_3$O$_3$: Calculated: C, 55,6%; H, 9,7%; N, 16,2% Found: C, 55,6%; H, 9,3%; N, 16,0%.

EXAMPLE 4

N-n-propyl-N'-(2-hydroxy-3-piperidino-propoxy)-urea

O-(2-hydroxy-3-piperidino-propyl)-hydroxylamine (1,74 g, 0,01 mol) was dissolved in 30 ml chloroform and under stirring 0,95 ml (0,01 mol) of n-propyl isocyanate was added thereto. After 1 hour, an additional 0,3 ml (3,17 mmol) n-propyl isocyanate was added and the mixture was stirred for an additional 1 hour. The solution was evaporated and the oil thus obtained purified by column chromatography.

Yield: 1,3 g (50%). IR (KBr): 3319, 2934, 2878, 2802, 1666, 1551, 1456, 1393, 1308, 1155, 1092, 1040, 993, 889, 793 cm$^{-1}$. $^1$H-NMR (DMSO-d$_6$): 8,98 (1H,s,NH); 6,95 (1H,t,J=5,8 Hz,CH$_2$N$\underline{H}$CO); 4,9 (1H, br,s,OH); 3,81 (1H, m,C$\underline{H}$OH); 3,74 (1H,dd,J=10,4 and =3,2 Hz, OCH$_2$); 3,56 (1H, dd,J=10,4 and =7,1 Hz,OCH$_2$); 3,05 (2H,q,J=6,4 Hz,C$\underline{H}_2$NH); 2,35 (4H,m, piperidine); 2,24 (2H,d,J=6,4 Hz,CHC$\underline{H}_2$N); 1,57–1,25 (6H,m,piperidine); 1,55–1,25 (2H,m, CH$_3$C$\underline{H}_2$); 0,84 (3H,t,J=7.4 Hz,CH$_3$). $^{13}$C-NMR (DMSO-d$_6$): 159,9 (s,CO); 79,1 (t,OCH$_2$); 65,2 (d,CHOH); 61,4 (t,CH$_2$N); 54,5 (t,piperidine); 40,3 (t,CH$_2$NH); 25,3 (e); 23,7 (t), es 22,7 (t)(CH$_3$$\underline{C}$H$_2$+piperidine); 11,0 (q,CH$_3$)$_2$.

The above compound was also be prepared by the following alternative process:

N-(2-hydroxy-3-piperidino-propoxy)-ethyl carbamate (2,46 g, 0,01 mol) was dissolved in 30 ml abs. tetrahydrofurane, 2,1 ml (0,015 mol) triethyl amine was added and subsequently 0,82 ml (0,59 g, 0,01 mol) n-propylamine in 10 ml abs. tetrahydrofurane was added dropwise while stirring. The mixture was boiled for 72 hours and then evaporated. The evaporation residue was purified by chromatography and the purified material was crystallized from petroleum ether thus obtaining the title compound. Yield: 2,4 g (65%).

EXAMPLE 5

N-cyclohexyl-N'-(2-hydroxy-3-piperidino-propoxy)-urea

O-(2-hydroxy-3-piperidino-propyl)-hydroxylamine (1,74 g, 0,01 mol) was dissolved in 40 ml abs. chloroform and 1,29 g (0,01 mol) cyclohexyl-isocyanate while stirring. After 24 hours the reaction mixture was evaporated and the residue crystallized with methanol. Yield: 2,0 g (67%). Mp.: 108–110° C. (from methanol).

IR (KBr): 3319, 3287, 3188, 2930, 2853, 2797, 1637, 1574, 1452, 1354, 1331, 1300, 1101, 1098, 991 cm$^{-1}$. $^1$H-NMR (DMSO-d$_6$): 8,75 (1H,s,CONHO); 6,52 (1H,d,J= 7,7 Hz, CHN$\underline{H}$CO); 4,71 (1H,s,CHO$\underline{H}$); 3,80 (1H,m,C$\underline{H}$OH); 3,76 (1H,dd,J=10,4 and =3,1 Hz,OCH$_2$); 3,57 (1H, dd,J=10,4 and =7,2 Hz,OCH$_2$); 3,45 (1H,m, C$\underline{H}$NH); 2,37 (4H,t,J=4,8 Hz), and 1,9–1,6 (4H,m)(piperidine); 1,6–1,3 (6H,m, piperidine); 1,3–1,1 (6H,m,cyclohexyl). $^{13}$C-NMR (DMSO-d$_6$): 159,2 (s,CO); 79,1 (t,OCH$_2$); 65,2 (d,CHOH); 61,3 (t,CH$\underline{C}$H$_2$N); 54,5 (t,piperidine); 47,4 (d,CHNH); 32,6 (t), 32,5 (t), 25,0 (t), 24,3 (t) and 23,7 (t)(cyclohexyl); 25,4 (t), 24,3 (t), and 23,7 (t) (piperidine). Analysis: C$_{12}$H$_{23}$N$_3$O$_3$·0,5 H$_2$O Calculated: C, 58,4%; H, 8,5%; N, 13,6%. Found: C, 58,8%; H, 9,3%; N, 13,7%.

EXAMPLE 6

N-n-hexyl-N'-(2-hydroxy-3-piperidino-propoxy)-urea

O-(2-hydroxy-3-piperidino-propyl)-hydroxylamine (1,85 g, 0,011 mol) was dissolved in 30 ml chloroform and 1,17 ml (0,011 mol) n-hexyl-isocyanate was added while stirring. After 3 hours the reaction mixture was evaporated and purified by column chromatography. The oil thus obtained crystallizes slowly in refrigerator and rubbing the crystals in petroleum ether a white material was obtained.

Yield: 0,9 g (27%). Mp.: 50–52° C.

IR (KBr): 3310, 2932, 2858, 2804, 1666, 1551, 1454, 1377, 1306, 1092, 1040, 995, 791, 725, 604 cm$^{-1}$. $^1$H-NMR (DMSO-d$_6$): 8,97 (1H,s,NH); 6,91 (1H,t,J=5,8 Hz,NH); 4,89 (1H,s,OH); 3.82 (1H,m,C$\underline{H}$OH); 3,72 (1H,dd,J=10,4 and =3,3 Hz, OCH$_2$); 3,56 (1H,dd,J=10,4 and =7,1 Hz,OCH$_2$); 3,05 (2H,q,C$\underline{H}_2$NH); 2,50 (4H,m,piperidine); 2,23 (2H,d,J=

6,4 Hz,CHC$\underline{H}_2$N); 1,55–1,3 (2H,m), and 1,27 (6H,m)((CH$_2$)$_4$, hexyl); 1,55–1.25 (6H,m,piperidine); 0,86 (3H,t,J=6,4 Hz,CH$_3$) $^{13}$C-NMR (DMSO-d$_6$): 159,8 (s,CO); 79,0 (t,OCH$_2$); 65,2 (d,CHOH); 61,4 (t,CH$\underline{C}$H$_2$N); 54,5 (t,piperidine); 38,5 (t,CH$_2$NH); 30,8 (t), 29,5 (t), 25,7 (t), and 21.8 (t)((CH$_2$)$_4$); 25,3 (t) and 23,7 (t)(piperidine); 13,7 (q,CH$_3$). Analysis: C$_{15}$H$_{31}$N$_3$O$_3$: Calculated: C, 59,8%; H, 10,4%; N, 13,9% Found: C, 60,0%; H, 10,1%; N, 13,9%.

EXAMPLE 7

N-(3-chlorophenyl)-N'-(2-hydroxy-3-piperidino-propoxy)-urea

O-(2-hydroxy-3-piperidino-propyl)-hydroxylamine (2,0 g, 11,48 mmol) was dissolved in 40 ml chloroform and 1,4 ml (11,48 mmol) 3-chlorophenyl-isocyanate was added thereto and stirred for 4 hours at ambient temperature. The reaction mixture was evaporated and purified by column chromatography. The chromatografically pure oil was crystallized from ether. Yield: 1,3 g (34%). Mp.: 117–118° C.

IR (KBr): 3250, 2939, 2900, 1670, 1597, 1551, 1491, 1429, 1329, 1252, 1119, 972, 775, 718, 700 cm$^{-1}$. $^1$H-NMR (DMSO-d$_6$): 9,7 (1H,s,CONHO); 9,3 (1H,s,NH); 7,7 (1H, br,s,), 7.44 (1H,d,J=8,0 Hz,), 7,30(1H,t,J=8,0 Hz,), and 7,05 (1H, d, J=8,0Hz), (phenyl); 5.35 (1H,s,OH); 4,0–3,8 (2H, m,C$\underline{H}$OH,OCH$_2$); 3,69 (1H,dd, J=10,7 and =7,9 Hz,OCH$_2$); 3,27 (2H,d,J=6,2Hz,CHCH$_2$N); 2,36 (4H,m), and 1,55–1,25 (6H,m)(piperidine). $^{13}$C-NMR (DMSO-d$_6$): 157,1 (s,CO); 140,4 (s), 132,9 (s), 130,1 (d), 121,9 (d), 117.9 (d), and 117,0 (d)(phenyl); 79,8 (t,OCH$_2$); 65,3 (d,CHOH); 61,2 (t,CH$\underline{C}$H$_2$N); 54.5 (t), 25,4 (t), and 23,7 (t) (piperidine). Analysis: C$_{15}$H$_{22}$ClN$_3$O$_3$.0,5 H$_2$O: Calculated: C, 53,9%; H, 6,9%; N, 12,5% Found: C, 53,9%; H, 6,8%; N, 12,3%.

EXAMPLE 8

N-methyl-N'-(2-hydroxy-3-piperidino-propoxy)-urea

O-(2-hydroxy-3-piperidino-propyl)-hydroxylamine (2,47 g, 0,0142 mol) was dissolved in 40 ml abs. chloroform and 0,84 ml (0,0142 mol) methyl isocyanate was added thereto while stirring. The mixture was stirred for 2 hours at 25° C. Subsequently, the solution was evaporated and the residue rubbed with ether. Yield: 2,5 g (76%). Mp.: 98–101° C.

IR (KBr): 3356, 3217, 2943, 1658, 1556, 1414, 1377, 1292, 1132, 1092, 984, 908, 779, 741, 636 cm$^{-1}$. $^1$H-NMR (DMSO-d$_6$): 9,0 (1H,s,CONHO); 6,91 (1H,q,J=4.5 Hz, CH$_3$N$\underline{H}$CO); 4,82 (1H,br,s,OH); 3,8 (1H,m,C$\underline{H}$OH): 3,7–3,5 (2H,dd,OCH$_2$); 2,62 (3H,d,CH$_3$N); 2.32 (m,4H, piperidine); 2,25 (2H,d,CHC$\underline{H}_2$N); 1,6–1,3 (6H,m, piperidine) $^{13}$C-NMR (DMSO-d$_6$): 160,4 (s,CO); 78,9 (t,OCH$_2$); 65,2 (d,CHOH); 61,5 (t,CH$_2$N); 54,5 (t,piperidine); 25,54 (q,CH$_3$N); 25,3 (t), and 23,7 (t) (piperidine). Analysis: C$_{10}$H$_{21}$N$_3$O$_3$: Calculated: C, 51,9%; H, 9,2%; N, 18,2% Found: C, 51,7%; H, 9,2%; N, 18,6%.

The above compound was prepared according to the following alternative method as well:

O-(2-hydroxy-3-piperidino-propyl)-hydroxylamine (1,74 g, 0,01 mol) was dissolved in 50 ml abs. chloroform and 0,94 g (0,01 mol) N-methyl carbamoyl chloride in 10 ml chloroform was added dropwise while stirring at 5° C. The mixture was stirred for 2 hours at room tempferature followed by washing with 2×30 ml 1n sodium hydroxide and 1×20 ml water. The chloroform layer was dried over magnesium sulfate, and after filtering off the drying agent the solution was evaporated. The residue was triturated with ether, thus obtaining the title compound. Yield: 1,9 g (82%).

EXAMPLE 9

N-tert.-butyl-N'-(2-hydroxy-3-piperidino-propoxy)-urea

O-(2-hydroxy-3-piperidino-propyl)-hydroxylamine (2,53 g 0.0145 mol) was dissolved in 40 ml abs. chloroform and 1,66 ml (0,0145 mol) ter.-butyl isocyanate was added thereto while stirring. The mixture was stirred for 2.5 hours. Subsequently, the solution was evaporated and the residue triturated with petroleum ether and then purified by column chromatography. The oil thus obtained was crystallized from petroleum ether. Yield: 1,5 g (38%). Mp.: 71–73° C.

IR (KBr): 3314, 2945, 2916, 1651, 1555, 1460, 1393, 1384, 1335, 1254, 1111, 988, 903, 839, 781 cm$^{-1}$. $^1$H-NMR (DMSO-d$_6$): 8,78 (1H,s,CONHO); 6,6 (1H,s,CNHCO); 4,9 (1H, bd,s,OH); 3,8 (1H,m,C$\underline{H}$OH); 3,55–3,45 (2H,dd, OCH$_2$); 2,3 (m,4H, piperidine); 2,25 (2H,d, CH$_2$N); 1,5–1,3 (6H,m,piperidine). $^{13}$C-NMR (DMSO-d$_6$): 159,2 (s,CO); 79,1 (t,OCH$_2$); 65,0 (d,CHOH); 61,2 (t,CH$_2$N); 54,5(t, piperidine); 49,2(s,(CH$_3$)$_3$$\underline{C}$); 28,6(q,($\underline{C}$H$_3$)$_3$C); 25,3(t), and 23,7(t)(piperidine). Analysis: C$_{13}$H$_{27}$N$_3$O$_3$: Calculated: C, 57,10%; H, 9,9%; N, 15,4% Found: C, 56,9%; H, 9,9%; N, 5,8%.

EXAMPLE 10

N-(4-methoxyphenyl)-N'-(2-hydroxy-3-piperidino-propoxy)-urea

O-(2-hydroxy-3-piperidino-propyl)-hydroxylamine (2,53 g, 0,0145 mol) was dissolved in 40 ml abs. chloroform and 1,9 ml (0,0145 mol) 4-methoxyphenyl isocyanate was added thereto while stirring. After 3 hours, the solution was evaporated and the residue was purified by column chromatography. The oil thus obtained was crystallized from diethyl ether.

Yield: 2,0 g (42%). Mp.: 103–104° C. IR(KBr): 3398, 3183, 3098, 2943, 2837, 1691, 1596, 1537, 1514, 1486, 1302, 1229, 982, 899, 831 cm$^{-1}$. $^1$H-NMR (DMSO-d$_6$): 9,4 (1H,s,CONHO); 8,9 (1H,s,N$\underline{H}$CONHO); 7,41 (2H,d) and 6,85 (2H,d)(phenyl), 5.25 (1H,br,s,OH); 3,85 (1H,m,C$\underline{H}$OH); 3,7 (3H,s,OCH$_3$); 3,83–3,5 (2H,dd,OCH$_2$); 2.33 (4H, m,piperidine); 2.29 (2H,d,CH$_2$N); 1,46–1.35 (6H,m, piperidine). $^{13}$C-NMR (DMSO-d$_6$): 157,6 (s,CO); 154,7 (s), 131,7 (s) 120,5 (d) and 113,6 (d)(phenyl); 79,6 (t,OCH$_2$); 65,3 (d,CHOH); 61,2 (t,CH$_2$N); 54,9 (q,OCH$_3$); 54,5 (t), 25,4 (t) and 23,8 (t) (piperidine). Analysis: C$_{16}$H$_{25}$N$_3$O$_4$: Calculated: C, 59,4%; H, 7,8%; N, 13,0% Found: C, 59,1%; H, 8,0%; N, 13,8%.

EXAMPLE 11

N-benzyl-N'-(2-hydroxy-3-piperidino-propoxy)-urea

O-(2-hydroxy-3-piperidino-propyl)-hydroxylamine (2,53 g, 0,0145 mol) was dissolved in 40 ml abs. chloroform and 1,8 ml (0,0145 mol) benzyl isocyanate was added thereto while stirring. The mixture was stirred for 2 hours, the solution was evaporated and the residue was crystallized from ethanol-ether mixture. Yield: 2,1 g (47%). Mp.: 100–101° C.

IR (KBr): 3320, 3000, 2910, 1660, 1530, 1370, 1190, 1155, 1125, 1105, 1085, 976, 780, 695 cm$^{-1}$. $^1$H-NMR (DMSO-d$_6$): 9,20 (1H,s,CONHO); 7,50 (1H,t,CH$_2$N$\underline{H}$CO); 7,32–7,22 (5H,m,phenyl); 4,9 (1H,br,s,OH), 4,30 (2H,d,J= 6,1Hz,CH$_2$NCO); 3,81 (1H,m,C$\underline{H}$OH); 3,75 (1H,dd,OCH$_2$); 3,63 (1H,dd,OCH$_2$); 2,34–2,2 (6H,m, C$\underline{H}_2$N); 1,44–1,33 (6H,m,piperidine) $^{13}$C-NMR (DMSO-d$_6$): 159,9 (s,CO);

140,0 (s); 127,9 (d), 126,6 (d), and 126,41 (d)(phenyl); 79,2 (t,OCH$_2$); 65,2 (s,CHOH); 61,5 (CH$\underline{C}$H$_2$N); 42,0 (t,Ph$\underline{C}$H$_2$N); 25,3 (t) and 23,7 (t)(piperidine). Analysis: C$_{16}$H$_{25}$N$_3$O$_3$: Calculated: C, 62,5%; H, 8,2%; N, 13,7% Found: C, 62,5%; H, 8,0%; N, 13,4%.

EXAMPLE 12

N-isopropyl-N'-[2-hydroxy-3-(4-benzyl-piperazino)-propoxy]-urea hydrochloride

O-[2-hydroxy-3-(4-benzyl-1-piperazino)-propyl]-hydroxylamine (2,65 g 0,01 mol was dissolved in 50 ml abs. chloroform, 1 ml (0,01 mol) isopropyl isocyanate was added thereto dropwise while stirring and stirring was continued for additional 3 hours. After the reaction the oil obtained was evaporated and 3,5 g oily material was obtained. The title compound was recovered from the oil by the addition of hydrochloric acid in ether. Yield: 2,4 g.

By recrystallizing the dihydrochloride (1 g) in ethyl acetate, 0.85 g of white crystalline material was obtained. Mp.: 208–212° C. (ethyl acetate, dec.).

IR (KBr): 3337, 3297, 3165, 2972, 2864, 1657, 1551, 1445, 1420, 1358, 951, 926, 746, 696 cm$^{-1}$. $^1$H-NMR (DMSO-d$_6$): 13–12 (1H,br,s,NH$^+$); 12–11 (1H,br,s, NH$^+$); 9,15 (1H,br,s, CONHO); 7,7 (2H,m) and 7,5 (3H, phenyl o,m+p); 6,72 (1H,d,J=8,0Hz,CHN$\underline{H}$CONH); 4,7–4,2 (3H, m,OCH$_2$CH); 3,9–3,0 (13H,m, C$\underline{H}$NH+CHC$\underline{H}_2$N+piperazine, NC$\underline{H}_2$-phenyl); 1,12 (6H,d,J=6,4 Hz, 2×CH$_3$). $^{13}$C-NMR (DMSO-d$_6$): 158,9 (s,NHCO); 131,2 (d), 129,3 (d), and 128,6 (d) (phenyl); 77,2 (t,OCH$_2$); 62,9 (d,CHOH); 40,6 (d,CHNH); 60–58, 50–46 (piperazine); 22,5 (q,CH$_3$). Analysis: C$_{18}$H$_{32}$N$_4$O$_3$.0,5 H$_2$O: Calculated: C, 50,0%; H, 7,7%; N, 12,9% Found: C, 50,2%; H, 7,6%; N, 13,2%.

EXAMPLE 13

N-tert-butyl-N'-(2-hydroxy-3-diethylamino-propoxy)-urea

O-(2-hydroxy-3-diethylamino-propyl)-hydroxylamine was dissolved in 40 ml abs chloroform and 3,08 ml (0,027 mol) tert-butyl isocyanate was added thereto dropwise. The mixture was stirred at room temperature for 15 hours and evaporated. The product thus obtained was purified by column chromatography. The material thus obtained is in oily form which crystallizes when storing in refrigerator. The crystals were filtered after trituration with petroleum ether. Yield: 1,44 g (20%). Mp.: 58–61° C.

IR (KBr): 3325, 2965, 2934, 1670, 1549, 1460, 1393, 1386, 1323, 1236, 1092, 1067, 991, 783 cm$^{-1}$. $^1$H-NMR (DMSO-d$_6$): 8,63 (1H,bd,s,CONHO); 6,35 (1H, bd, s, (CH$_3$)$_3$CN$\underline{H}$CO); 3,81 (1H,dd,J=11,2 and =2,9 Hz,OCH$_2$); 3,60 (1H,dd, J=11,2 and =8,1 Hz,OCH$_2$); 3,8–3,7 (1H,m,C$\underline{H}$OH, overlapping); 2,55 (4H,q,J=7,2 Hz,C$\underline{H}_2$CH$_3$); 2,42 (2H,d,J= 6.3 Hz,CHC$\underline{H}_2$N); 1,32 (9H,s, (CH$_3$)$_3$C); 0,97 (6H,t,J=7,2 Hz,CH$_2$C$\underline{H}_3$). $^{13}$C-NMR (DMSO-d$_6$): 159,2 (s,NHCO); 79,0 (t,OCH$_2$); 65,9 (d,CHOH); 55,5 (t,CHC$\underline{H}_2$N), 49,2(s, (CH$_3$)$_3$$\underline{C}$); 47,0(t,2×N$\underline{C}$H$_2$CH$_3$); 28,6 (q, ($\underline{C}$H$_3$)$_3$$\underline{C}$); 11,5 (q,CH$_2$$\underline{C}$H$_3$).

EXAPLE 14

N'-(2-hydroxy-3-piperidino-propoxy)-benzyl carbamate

O-(2-hydroxy-3-piperidino-propyl)-hydroxylamine (1,74 g, 0,01 mol) was dissolved in 40 ml abs. chloroform and 1,41 ml (0,01 mol) benzyl chloroformiate in 10 ml chloroform was added thereto dropwise at 0° C. The mixture was stirred at 20° C. for 4 hours and another portion of 1,41 ml (0,01 mol) benzyl chloroformiate was added and stirred for additional 2 hours. To the reaction mixture 1,4 ml (0,01 mol) triethylamine was added and stirred for 4 hours followed by evaporating and purifying the oily residue by column chromatography. Thus, a light yellow oil was obtained. Yield: 1,62 g (53%).

$^1$H-NMR (DMSO-d$_6$): 10,4 (1H,br,s,NH); 7,35–7,3 (5H, m,phenyl); 5,1 (2H, PhC$\underline{H}_2$O): 4,5 (1H,d,CHO$\underline{H}$); 3,81–3,6 (3H,m,OCH$_2$+C$\underline{H}$OH); 2,4–2,2 (6H,m), and 1,4–1,2 (6H,m) (piperidine). $^{13}$C-NMR (DMSO-d$_6$): 156,7 (s,CO); 142,3 (s); 128,2 (d), 127,8 (d), 127,7 (d), 126,4 (d), and 126,2 (d)(phenyl); 79,2 (t,OCH$_2$); 65,7 (t, PhC$\underline{H}_2$O); 65,3 (d,CHOH); 61.5 (t,CH—$\underline{C}$H$_2$N); 54,5 (t), 25,3 (t), es 23,69 (t) (piperidine).

The title compound was prepared by the following alternative method as well:

3,1 g (0,02 mol) N-hydroxy-carbamic acid benzyl ester and 2,24 g (0,04 mol) sodium hydroxide were dissolved in the mixture of 10 ml water and 3 ml dimethyl sulfoxide. 3,1 ml (3,7 g, 0,04 mol) epichlorohydrine was added to the solution while stirring at 0° C. and the mixture was stirred for 8 hours at this temperature. 20 ml water was added followed by extraction with 4×20 ml ethyl acetate, the combined ethyl acetate layers were washed with 1×20 ml water, dried over magnesium sulfate, filtered and the solution evaporated. The oil thus obtained was dissolved in 40 ml diethyl ether, 19,7 ml (17 g, 0,2 mol) piperidine and 15 ml of 4N sodium hydroxide were added thereto. The mixture was boiled for 5 hours, the layers separated, the ether layer washed with 2×20 ml saturated saline solution, dried over magnesium sulfate and evaporated. The oily residue was purified by column chromatography to obtain the title compound. Yield: 4,1 g (67%).

EXAMPLE 15

N-cyclohexyl-N'-{2-hydroxy-3-[N-(cyclohexyl-carbamoyl)-N-tert-butylamino]-propoxy}-urea O-(2-hydroxy-3-tert-butylamino-propyl)-hydroxylamine (2,65 g, 0,01812 mol) was dissolved in 50 ml abs. chloroform and 4,6 ml (0,3624 mol) cyclohexyl isocyanate was added thereto while stirring. The mixture was stirred for 2 hours at room temperature and evaporated. The residue was dissolved in ethyl acetate, treated with charcoal, followed by filtering and evaporating the solution. The light yellow oil thus obtained was crystallized from the mixture of ethyl acetate and ether. Yield: 3,3 g (44%). Mp.: 151–152° C.

IR (KBr): 3312, 2932, 2854, 1668, 1616, 1555, 1450, 1393, 1364, 1354, 1252, 1220, 1130, 941, 891 cm$^{-1}$. $^1$H-NMR (DMSO-d$_6$): 9,01 (1H,s,CONHO); 6,68 and 6,64 (1H,d,J=8.7 Hz; 1 H,d, J=8,1 Hz,2×CHN$\underline{H}$); 6,25 (1H,d,J= 4,3 Hz,OH); 3,75 (1H,m,C$\underline{H}$OH); 3,70 (1H,dd, J=10,2 and =3,5 Hz) and 3,55 (1H,dd,J=10,2 and =7,0 Hz)(OC$\underline{H}_2$CH); 3,40 (2×1H, m,cyclohexyl); 3,25 (1H,d,J=16,0 Hz) and 3,00 (1H,dd,J=16,0 Hz,J=8,6 Hz) (CHC$\underline{H}_2$N); 1,8–1,4 (2×4H, m, cyclohexyl); 1,29 (9H,s,CH$_3$); 1,4–0,9 (2×6H,m, cyclohexyl). $^{13}$C-NMR (DMSO-d$_6$): 159,3 (s), and 159,0 (s)(CO); 78,1 (t,OCH$_2$); 70,4 (d,CHOH); 54,9 (s,$\underline{C}$(CH$_3$)$_3$); 48,1 (t,CHC$\underline{H}_2$N); 44,6 (d), and 44,5 (d) (cyclohexyl); additional signals: 33,0 (t); 32,7 (t); 32,6 (t); 28,4 (q,CH$_3$); 25,2 (t); 25,0 (t); 24,3 (t); 24,1 (t).

The title compound was prepared by the following alternative method as well:

N-cyclohexyl-N'-(2-hydroxy-3-N-tert-butylamino-propoxy)-urea (2,88 g, 0.01 mol) was dissolved in 50 ml abs. chloroform and 1,25 g (0,01 mol) cyclohexyl isocyanate was added thereto while stirring. The mixture was stirred for 2 hours at room temperature and evaporated. The residue was dissolved in ethyl acetate, treated with charcoal, followed by filtering and evaporating the solution. The residual oil thus obtained was crystallized from the mixture of ethyl acetate and ether thus obtaining the title compound. Yield: 3,1 g (75%)

EXAMPLE 16

N-n-hexyl-N'-(3-piperidino-propoxy)-urea

O-(3-piperidino-propyl)-hydroxylamine (1,37 g, 8,66 mmol) was dissolved in 25 ml abs chloroform and 0,92 g (8,66 mmol) n-hexyl isocyanate was added thereto while stirring. The reaction was followed by chromatography. After one day, an other portion of n-hexyl isocyanate (0,46 ml, 4,33 mmol) was added and the mixture was stirred for 2 hours. The chloroform layer was washed with 20 ml 10% sodium carbonate solution and 1×2 ml water, dried over magnesium sulfate, filtered and the solution was evaporated. Yield: 2,1 g (85%).

IR (KBr): 3354, 2932, 2856, 2810, 2777, 1666, 1543, 1486, 1377, 1308, 1155, 1134, 1076 cm$^{-1}$. $^1$H-NMR (CDCl$_3$): 8,12 (1H,br,s,NH); 6,3 (1H,t,J=5,6 Hz,CH$_2$NHCO): 3.85 (2H,t,J=5,9 Hz,OCH$_2$); 3,27 (2H,dd,J=7,1 and =5,6 Hz,C$\underline{H}_2$NH); 2.3 (6H,m, piperidine); 1,85 (2H,m, OCH$_2$C$\underline{H}_2$CH$_2$); 1,7–1,2 (14H,m, piperidine+CH$_3$(C$\underline{H}_2$)$_4$); 0,92 (3H,t,J=6,7 Hz,CH$_3$). $^{13}$C-NMR (CDCl$_3$): 160,3 (s,CO); 76,5 (t,OCH$_2$); 56,2 (t, OCH$_2$CH$_2$C$\underline{H}_2$N); 54,4 (t,piperidine); 39,5 (t,CH$_2$NH); 31,4 (t), 30,2 (t), 26,4 (t), 25,6 (t), 25,4 (t), 24,2 (t), and 22,4 t) (piperidine+OCH$_2$C$\underline{H}_2$CH$_2$+CH$_3$(CH$_2$)$_4$); 13,8 (q,CH$_3$).

EXAMPLE 17

N-cyclohexyl-N'-(2-acetoxy-3-piperidino-propoxy)-urea hydrochloride

N-cyclohexyl-N'-(2-hydroxy-3-piperidino-propoxy)-urea (0,67 g, 2,238 mol) was dissolved in 25 ml abs. chloroform and 0,23 ml (2,462 mmol) acetic anhydride was added thereto while stirring. The mixture was stirred overnight followed by evaporation. The hydrochloride salt was prepared from the oil obtained with hydrochloric acid in ether. Yield: 0,56 g (66%). Mp.: 184–186° C.

IR (KBr): 3381, 3211, 2935, 2854, 2739, 2664, 2548, 1744, 1730, 1672, 1531, 1450, 1371,1242, 1229 cm$^{-1}$. $^1$H-NMR (DMSO-d$_6$): 10,7 (1H,br,s, NH$^+$); 9,2 (1H,s, CONHO); 6,62 (1H,d,J=8,2 Hz,CNHCO); 5,38 (1H,m, CHO—CO); 3,87 (2H,d,J=4,7 Hz, OCH$_2$); 3,4 (5H,m); 2,9 (2H,m); 2,12 (3H,s,COCH$_3$); 2,0–1,4 (10H,m); 1,45–0,95 (6H,m) $^{13}$C-NMR (DMSO-d$_6$): 169,7 (s,C̲OCH$_3$); 158,7 (s,CO); 74,3(t,OCH$_2$); 65,9 (d, C̲HOCO); 55,8 (t), 52,9 (t), 52,1 (t), 47,8 (d,2×cyclohexyl); 24,5 (t), 21,7 (t), 21,0 (q,CH$_3$).

EXAMPLE 18

N-cyclohexyl-N'-acetyl-N'-(2-acetoxy-3-piperidino-propoxy)-urea

N-cyclohexyl-N'-(2-hydroxy-3-piperidino-propoxy)-urea (1,2 g, 4,01 mmol) was dissolved in 10 ml (0,106 mol) acetic anhydride, 0,1 ml pyridine was added and the mixture was allowed to stand overnight at room temperature. The mixture was then evaporated, dissolved in 30 ml chloroform, followed by washing the chloroform layer with 10 ml 10% sodium carbonate solution and 1×20 ml water, dried over magnesium sulfate, filtered and evaporated. Yield: 1,2 g.

IR (KBr): 3296, 2934, 2854, 2787, 1730, 1660, 1520, 1452, 1371, 1317, 1236, 1040, 891, 750, 621 cm$^{-1}$. $^1$H-NMR (DMSO-d$_6$): 7,93 (1H,d,J=7,8 Hz,NH); 5,13 (1H, m,CHO); 4,18 (1H,dd,J=9.9 and =2.9 Hz) and 4,08 (1H,dd, J=9,9 and =6.3 Hz)(NOCH$_2$); 3.54 (1H,m,cyciohexyl CH); 2,5–2,3 (6H,m,CH$_2$N, piperidine); 2,27 (3H,s,NCOCH$_3$); 2,02 (3H,s,OCOCH$_3$); 1,9–1,1 (16H,m, cxclohexyl+piperidine). $^{13}$C-NMR (DMSO-d$_6$): 171,8 (s,NC̲OCH$_3$); 169,5 (s,OC̲OCH$_3$); 150,0 (s,NHCON); 75,0 (t,OCH$_2$); 68,5 (d,CHOH); 57,7 (t,CHC̲H$_2$N); 54,2 (t,piperidine); 48,5 (d,CHNH); 31,9 (t,cyclohexyl); signals of the two rings: 25,3 (t); 24,8 (t); 24,0 (t); 23,6 (t) (cyclohexyl+piperidine); 22,9 (q) and 20,7 (q)(C̲H$_3$COO and C̲H$_3$CON).

EXAMPLE 19

N-(3-nitrophenyl)-N'-(2-hydroxy-3-piperidino-propoxy)-urea

O-(2-hydroxy-3-piperidino-propyl)-hydroxylamine (1,74 g, 0,01 mol) was dissolved in 25 ml abs. chloroform and 1,64 g (0,01 mol) 3-nitrophenyl isocyanate in 20 ml abs. chloroform was added thereto while stirring. After 1 hour reaction the mixture was evaporated and purified by column chromatography. The oil thus obtained was crystallized from diethyl ether. Yield: 1,84 g (54%). Mp.: 137–139° C.

IR (KBr): 3281, 2943, 2818, 1672, 1607, 1560, 1529, 1486, 1437, 1354, 1283, 1115, 802, 739 cm$^{-1}$. $^1$H-NMR (DMSO-d$_6$): 9,87 (1H,br,s) and 9,55 (1H,br,s)(2×NH), 8,57 (1H,t,J=2,1 Hz), 7,91 and 7,85 (2×1H,dd,J=8,2 and =2,1 Hz), 7,58 (1H,t,J$_1$=J$_2$=8,2 Hz)(phenyl); 5,16 (1H,br,s,OH); 3,95 (1H,m,C̲HOH); 3,88 (1H,dd,J=10,5 and =3,0 Hz) and 3,71 (1H,dd,J=10,5 and =7,4 Hz)(OCH$_2$); 2,36(4H,m, piperidine); 2,30 (2H,d,J=6,3 Hz,CHC̲H$_2$N); 1,46 (4H,m), and 1,36 (2H,m)(piperidine). $^{13}$C-NMR (DMSO-d$_6$): 157,0 (s,CONH); 147,8, 140,2, 129,7, 124,7, 116,7, and 112,6 (phenyl); 79,8 (t,OCH$_2$); 65,4 (d,CHOH); 61,2 t, CHC̲H$_2$N); 54,5(t), 25,3 (t), and 23,7 (t)(piperidine).

EXAMPLE 20

N-n-hexyl-N'-(2-hydroxy-3-morpholino-propoxy)-urea maleate

O-(2-hydroxy-3-morpholino-propyl)-hydroxylamine (1,76 g, 0,01 mol) was dissolved in 25 ml abs. chloroform and 1,06 ml (0,01 mol) n-hexyl isocyanate was added thereto while stirring. The reaction was followed by chromatography. After one hour, an additional portion of 0,5 ml (5 mmol) n-hexyl isocyanate was added and the mixture was stirred for 2 hours. The chloroform layer was washed with 20 ml 10% sodium carbonate solution and 1×20 ml water, dried over magnesium sulfate, filtered and evaporated. The oil thus obtained (2,57 g) was dissolved in 15 ml ethyl acetate and isolated in the salt form by the addition of equivalent amount (0,98 g) of maleic acid. Yield: 2,55 g (61%). Mp.: 107–108° C. (ethyl acetate)

IR (KBr): 3402, 2932, 2860, 1655, 1576, 1493, 1387, 1366, 1194, 1136, 1076, 993, 876, 866, 710, 559 cm$^{-1}$. $^1$H-NMR (DMSO-d$_6$): 9,1 (1H,s,CONHO); 6,87 (1H,t,J=5,7 Hz, CH$_2$NH̲CO); 6,1 (2H,s,maleic acid CH); 4,10 (1H,m,C̲HOH); 3,80 (2×2H,m, morpholine); 3,67 (2H,d,J=5,4 Hz,OCH$_2$); 3,2–2,9 (8H,m, CH(OH)C̲H$_2$N+CH$_3$(CH$_2$)$_4$C̲H$_2$+morpholine); 1,42 (2H,m, CH$_3$(CH$_2$)$_3$C̲H$_2$); 1,25 (6H, br, C$\underline{H}_3$(C$\underline{H}_2$)$_3$); 0,93 (3H,t,J=6,5 Hz,CH$_3$). $^{13}$C-NMR (DMSO-d$_6$): 167,0 (s,maleic acid COOH); 159,7 (s,CONH); 135,1(d,maleic acid CH); 77,5 (t,OCH$_2$); 63.1 (t,morfoline); 62.6 (d,CHOH); additional signals: 58,6 (t) and 51,8 (t)(2× NCH$_2$); 38,6 (t), 30,7 (t), 29,4 (t), 25,7 (t), 21,8 (t), and 13,6 (q)(hexyl).

EXAMPLE 21

N,N-diphenyl-N'-(2-hydroxy-3-piperidino-propoxy)-urea

O-(2-hydroxy-3-piperidino-propyl)-hydroxylamine (0,92 g, 5,28 mmol) was dissolved in 20 ml abs. chloroform and 1,1 ml (7,92 mmol triethylamine was added thereto followed by the dropwise addition of 1,22 g (5,28 mmol) diphenyl carbamoyl chloride in 15 ml tetrahydrofurane. The mixture was stirred for 72 hours, the solid salt precipitated was filtered off and the solution evaporated. The evaporation residue was dissolved in chloroform, washed with 2×50 ml 10% sodium carbonate solution and 2×50 ml water, the organic phase was dried over magnesium sulfater evaporated and purified by chromatography. The oil thus obtained was crystallized from petroleum ether. Yield: 1,2 9 (61%). Mp.: 75–78° C.

IR (KBr): 3425, 3225, 2932, 2853, 2800, 1645, 1595 1491, 1450, 1348, 1119, 957, 874, 764, 702 cm$^{-1}$. $^1$H-NMR (DMSO-d$_6$): 9,50 (1H,br,s,CONHO); 7,35 (4H,m), and 7,20 (6H,m)(phenyl o,m+p); 4,7 (1H,br,s,OH); 3,9–3.5 (3H,m, OCH$_2$CH); 2,4–2,1 (6H,m, piperidine, CHC$\underline{H}_2$N); 1,55–1, 25 (6H,m, piperidine). $^{13}$C-NMR (DMSO-d$_6$): 157,5 (s,CO); 142,7 (s), 129,6, 127,6, and 126,5 (phenyl): 79,5 (t,OCH$_2$); 66,0 (d,CHOH); 62,0 (t,CH—C$\underline{H}_2$—N); 55,1 (t), 25,0 (t), and 24,3 (t)(piperidine).

EXAMPLE 22

N-(3-piridyl)-N'-(2-hydroxy-3-piperidino-propoxy)-urea 4,2 g (0,0284 mol) nicotic azide was boiled for 8 hours in toluene under nitrogen and after the addition of 4,95 g (0,0284 mol) O-(2-hydroxy-3-piperidino-propyl)-hydroxylamine boiling was continued for one hour. The solvent was distilled off and the residue was purified by column chromatography. The oil thus obtained was crystallized from the mixture of ether and petroleum ether. Yield: 1,2 g (14%). Mp.: 118–120° C.

$^1$H-NMR (DMSO-d$_6$): 9,78 and 9,32 (2×1H,br,s,NH); 8,67 (1H,d,J=2,4 Hz,piridine-2-H); 8,21 (1H,dd,J=4,7 and =1,5 Hz,piridine-6-H); 7,97 (1H,ddd,J=8,3, 2,4 and 1,5 Hz, piridine 4-H); 7,32 (1H,dd,J=8,3 and =4,7 Hz, piridine-5-H); 5,36 (1H,br,s,OH); 3,95 (1H,m,CH); 3,92 (1H,dd,J=10,6 and =3,0 Hz) and 3,70 (1H,dd,J=10,6 and =7,5 Hz)(OCH$_2$); 2,40 (4H,m,piperidine); 2,30 (2H,d,J=6,4 Hz,CHC$\underline{H}_2$N), 1,55–1,25 (6H,m,piperidine). $^{13}$C-NMR (DMSO-d6): 157,3 (s,CO); 143,3 and 140,5 (2×d,piridine-2-6-C); 135,5 (s,piridine-3-C); 125,6 and 123,3 (2×d,piridine-4-5-C); 79,8 (t,OCH$_2$); 65,3 (d,CHOH); 61,2 (t,CHC$\underline{H}_2$); 54,5 (t), 25,3 (t) and 23,8 (t)(piperidine).

EXAMPLE 23

N-heptyl-N'-(2-hydroxy-3-piperidino-propoxy)-urea

O-(2-hydroxy-3-piperidino-propyl)-hydroxylamine (1,23 g, 7,08 mmol) was dissolved in 30 ml abs. chloroform and 1,00 g (7,08 mmol) heptyl isocyanate was added thereto dropwise while stirring. The mixture was stirred for 24 hours at room temperature and evaporated. The oily material thus obtained crystallizes while storing in refrigerator. The crystals were triturated with petroleum ether and the white solid material was filtered. Yield: 1,8 g (80,6%). Mp.: 49–51° C.

$^1$H-NMR (CDCl$_3$): 7,62 (1H,br,s,CONHO); 6,74 (1H,t, J=5,3 Hz,CH$_2$—N$\underline{H}$CO); 4,2–3,3 (1H,br,s,OH); 3,98 (1H, m,C$\underline{H}$OH); 3,85 (1H,dd,J$_1$=11,1 Hz,J$_2$=2,2 Hz,OC$\underline{H}_2$); 3,68 (1H,dd,J$_1$=11,1 Hz,J$_2$=7,4 Hz, OC$\underline{H}_2$); 3,25 (2H,m,C $\underline{H}_2$—NH); 2,7–2,2 (6H,m,piperidine-DH$_2$ and piperidine-N—CH$_2$); 1,7–1,2 (10H,m,(CH$_2$)$_5$); 1,7–1,2 (6H,m, piperidine); 0,88 (3H,t,J=6,6 Hz,CH$_3$). $^{13}$C-NMR (CDCl$_3$): 161,0 (s,CONH); 79,0 (t,OCH$_2$); 64.0 (d,CHOH); 60,0 (t,CH(OH)C$\underline{H}_2$); 54,5 (t,piperidine-NCH$_2$); 39,6 (t,CH$_2$NH); 31,7 (t); 29,7 (t); 28,9 (t); 26.7 (t); 25,9 (t); 24,0 (t); 22,5 (t); (piperidine, —(C$\underline{H}_2$)$_5$—); 14,0 (q,CH$_3$).

EXAMPLE 24

N-octyl-N'-(2-hydioxy-3-piperidino-propoxy)-urea

O-(2-hydroxy-3-piperidino-propyl)-hydroxylamine (1,74 g, 10,0 mmol) was dissolved in 30 ml abs. chloroform and 1,55 g (10,0 mmol) octyl isocyanate was added thereto while stirring. The mixture was stirred for 24 hours at room temperature and evaporated, followed by purifying by column chromatography. The material was crystallized by triturating with petroleum ether and the white solid product filtered off. Yield: 2,27 g (68,7%). Mp.: 55–56° C.

$^1$H-NMR (CDCl$_3$): 7,72(1H,s,NH); 6,73(1H,t,J=5,3 Hz, NH), 4,4–3,6 (1H,s,OH); 3,97(1H,m,C$\underline{H}$OH); 3,88(1H,dd, J$_1$=11,1 Hz, J$_2$=2,4 Hz, OCH$_2$); 3.67 (1H,dd, J$_1$=11,1 Hz, J$_2$=7,5 Hz, OCH$_3$); 3,23 (2H,m,C$\underline{H}_2$NH); 2,57 (2H,m,CHC $\underline{H}_2$N); 2,4–2,1 (4H,m,piperidine); 1,7–1,2 (6H,m, piperidine); 1,7–1,2 (12H,m,CH$_3$(C$\underline{H}_2$)$_6$CH$_2$NH); 0.87 (3H, t,J=6,8 Hz,CH$_3$). $^{13}$C-NMR (CDCl$_3$): 161,1(s,CO); 79,0(t, OCH$_2$), 64,1(d,CHOH); 59,8(t,CHC$\underline{H}_2$N); 54,5(t, piperidine); 39,6(t,CH$_2$NH); 31,7(t); 29,7(t); 29,2(t); 29,1(t); 26,8(t); 25,9(t); 24,1(t); 22,6(t) (piperidine and CH$_3$(C $\underline{H}_2$)$_6$CH$_2$NH; 14,0(q,CH$_3$).

The following compounds were prepared substantially by the same method as described in Example 24:

EXAMPLE 25

N-pentyl-N'-(2-hydroxy-3-piperidino-propoxy)-urea

Yield: 85,5%, Mp.: 63–65° C.

EXAMPLE 26

N-pentyl-N'-(3-piperidino-propoxy)-urea (by using O-(3-piperidino-propyl)-hydroxylamine as starting material) Yield: 70,8%.

$^1$H-NMR (CDCl$_3$): 8,05(1H,br,s,NH); 6,3(1H,t,J=5,6 Hz,CH$_2$$\underline{H}$CO); 3,85(2H,t,J=OCH$_2$); 3,25(2H,dd,C$\underline{H}_2$NH); 2,3(6H,m,piperidine); 1,85(2H,m,OCH$_2$C$\underline{H}_2$CH$_2$); 1,7–1,2 (12H,m, piperidine+CH$_3$(C$\underline{H}_2$)$_3$); 0,9(3H,t,CH$_3$). $^{13}$C-NMR (CDCl$_3$): 160,3 (s,CO), 75,0(t,OCH$_2$); 56,2(t,OCH$_2$CH$_2$ $\underline{C}$H$_2$N); 54,4(t, piperidine); 39,6(t,CH$_2$NH); 29,9(t), 29,0(t); 25,4(t); 25,4(t); 25,3(t); 24,1(t); 22,3(t), (piperidine-OCH$_2$ $\underline{C}$H$_2$CH$_2$—CH$_3$(C$\underline{H}_2$)$_3$); 13,9(q,CH$_3$).

EXAMPLE 27

N-(3-trifluoromethyl-phenyl)-N'-(2-hydroxy-3-piperidino-propoxy)-urea

Yield: 60.9%, Mp.: 108–110° C.

We claim:

1. Hydroxylamine derivatives represented by the formula (I),

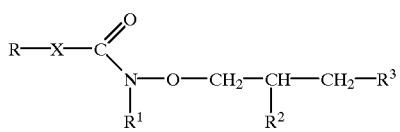

and the pharmaceutically acceptable acid addition salts thereof wherein X is O, —NH or a group of the formula —NR'—, wherein R and R', independently from each other, are alkyl, cycloalkyl, phenylalky; a phenyl group optionally sutbstituted with halo, haloalkyl, alkly, alkoxy or nitro; or an N-containing hetero ring, $R^1$ is H or alkanoyl, $R^1$ is H or hydroxy optionally acylated with alkanoyl, and $R^1$ is a group of the formula —N($R^1$)$R^1$ wherein $R^1$ is $R^2$, independently from each other, may be H, alkyl or a group of the formula —C(O)—NH—R wherein R is as defined above, or, $R^4$ and $R^5$, when taken together with the adjacent nitrogen attached thereto, form a 5 to 7-membered hetero ring which may contain one additional hetero atom selected from nitrogen, oxygen and sulfur and which is optionally substituted with alkyl of phenylalkyl.

2. Compounds of the formula (I) according to claim 1 wherein X is O and R, R', $R^1$, $R^2$, and $R^3$ are as defined in claim 1.

3. Compounds of the formula (I) according to claim 1 wherein X is NH or —NR' and R, R', $R^1$, $R^2$, and $R^3$ are as defined in claim 1.

4. Compounds of the formula (I) according to any of the claims 1 to 3 wherein the —N($R^4$)$R^5$ group standing for $R^3$ is optionally substituted
piperidino,
piperazino or morpholino.

5. Compounds of the formula (I) according to any of the claims 1 to 3 wherein the —N($R^4$)$R^5$ group standing for $R^3$ is dialkylamino.

6. Compounds of the formula (I) according to any of the claims 1 to 3 wherein the $R^3$ is —N($R^4$)$R^5$ and $R^4$ is alkyl and $R^5$ is —C(=O)—NH—R.

7. Pharmaceutical composition comprising as active substance a compound of the formula (I) as defined in any of claims 1 to 6 or the pharmaceutically active acid addition salts thereof.

8. Process for preparing hydroxylamine derivatives represented by the formula (I),

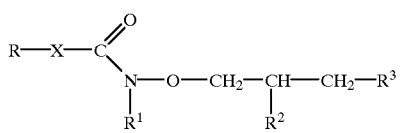

and the pharmaceutically acceptable acid addition salts thereof wherein

X is O, —NH or a group of the formula —NR'—, wherein

R and R', independently from each other, are alkyl, cycloalkyl, phenylalky; a phenyl group optionally sutbstituted with halo, haloalkyl, alkly, alkoxy or nitro; or an N-containing hetero ring, $R^1$ is H or alkanoyl, $R^2$ is H or hydroxy optionally acylated with alkanoyl, and $R^3$ is a group of the formula —N($R^4$)$R^5$ wherein $R^4$ is $R^5$, independently from each other, may be H, alkyl or a group of the formula —C(O)—NH—R wherein R is as defined above, or, $R^4$ and $R^5$, when taken together with the adjacent nitrogen attached thereto, from a 5 to 7-membered hetero ring which may contain one additional hetero atom selected from nitrogen, oxygen and sulfur and which is optionally substituted with alkyl of phenylalkyl, characterized in that a) for preparing compounds of the formula (I) wherein X is O, i) a compounds of the formula (II)

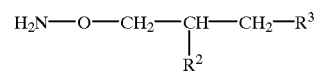

wherein $R^2$ and $R^3$ are as defined above, is reacted with a compound of the formula (III)

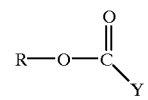

wherein R is as defined above and Y is halo or azido, or ii) a compound of the formula (VI)

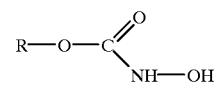

is reacted with a compound of the formula (VII)

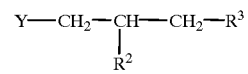

or iii) a compound of the formula (VI) is reacted with a compound of the formula (VIII)

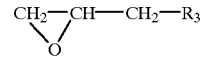

or iv) a compound of the formula (VI) is reacted with a compound of the formula (IX)

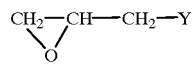
(IX)

and subsequently with a compound of the formula R'H, wherein in the formulae (VI), (VII), (VIII) and (IX) R, $R^2$ and $R^3$ are as defined above and Y is halo, b) for preparing compounds of the formula (I) wherein X is —NH—, a compound of the formula (II) wherein $R^2$ and $R^3$ are as defined above, is reacted with a compound of the formula (IV) or (IVa)

(IV)

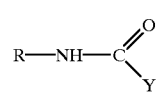
(IVa)

wherein R is as defined above and Y is halo, or c) for preparing compounds of the formula (I) wherein X is —NH—, or —NR'—, a compound of the formula (X)

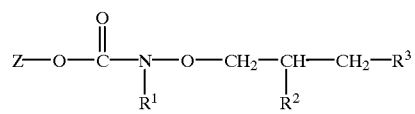
(X)

wherein $R^1$, $R^2$ and $R^3$ are as defined above and Z is alkyl, aralkyl or optionally substituted aryl, is reacted with a compound of the formula $RNH_2$ or RR'NH, wherein R and R' are as defined above, or d) for preparing compounds of the formula (I) wherein X is —NH—, $R^3$ is —N($R^4$)$R^5$, $R^4$ is alkyl and $R^5$ is —C(O))—NH—R, i) a compound of the formula (II) wherein $R^3$ is —N($R^4$)$R^5$, $R^4$ is alkyl and $R^5$ is H, and $R^2$ is a defined above, is reacted with an excess of a compound of the formula (IV) or (IVa) wherein R is as defined above and Y is halo, or ii) a compound of the formula (I) wherein $R^3$ is —N($R^4$)$R^5$, $R^4$ is alkyl and $R^5$ is H, $R^1$, $R^2$ and $R^3$ are as defined above, is reacted with a compound of the formula (IV) or (IVa) wherein R is as defined above and Y is halo, or e) for preparing compounds of the formula (I) wherein X is —NR'—, a compound of the formula (II) is reacted with a compound of the formula (V)

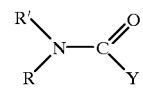
(V)

* * * * *